(12) United States Patent
Kim et al.

(10) Patent No.: US 10,265,038 B2
(45) Date of Patent: Apr. 23, 2019

(54) X-RAY PHOTOGRAPHING DEVICE COMPRISING VARIABLE TYPE ARM

(71) Applicants: VATECH Co., Ltd., Gyeonggi-do (KR); VATECH EWOO Holdings Co., Ltd., Gyeonggi-do (KR)

(72) Inventors: Tae Woo Kim, Gyeonggi-do (KR); Seung Hun Shin, Gyeonggi-do (KR); Keong Tae Yeom, Gyeonggi-do (KR); Byung Jik Lim, Gyeonggi-do (KR); Jin Pyo Chun, Gyeonggi-do (KR); Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 288 days.

(21) Appl. No.: 15/113,793

(22) PCT Filed: Jan. 23, 2015

(86) PCT No.: PCT/KR2015/000761
§ 371 (c)(1),
(2) Date: Jul. 22, 2016

(87) PCT Pub. No.: WO2015/111968
PCT Pub. Date: Jul. 30, 2015

(65) Prior Publication Data
US 2016/0338657 A1    Nov. 24, 2016

(30) Foreign Application Priority Data

Jan. 23, 2014  (KR) ..................... 10-2014-0008507
Jan. 23, 2014  (KR) ..................... 10-2014-0008568
(Continued)

(51) Int. Cl.
*A61B 6/00*     (2006.01)
*A61B 6/14*     (2006.01)

(52) U.S. Cl.
CPC .............. *A61B 6/4452* (2013.01); *A61B 6/14* (2013.01); *A61B 6/4429* (2013.01); *A61B 6/4458* (2013.01)

(58) Field of Classification Search
CPC ....... A61B 6/14; A61B 6/4429; A61B 6/4452; A61B 6/4458; H01J 35/065
(Continued)

(56) References Cited

U.S. PATENT DOCUMENTS 3,644,735 A * 2/1972 Vandervelden .......... A61B 6/14
                                                      378/197
4,101,779 A * 7/1978 Schmedemann ...... A61B 6/447
                                                      248/157
(Continued)

FOREIGN PATENT DOCUMENTS

JP       08-215324 A    8/1996
KR    10-2006-0118852 A  11/2006
(Continued)

OTHER PUBLICATIONS

European Patent Office, Extended European Search Report of corresponding EP Patent Application No. 15740308.0, Feb. 13, 2018.

*Primary Examiner* — Allen C. Ho
(74) *Attorney, Agent, or Firm* — IP Legal Services, LLC

(57) ABSTRACT

The present invention relates to an X-ray photographing device and, more specifically, to an X-ray photographing device comprising a variable type arm which can irradiate, without limitation of location or direction, X-rays to a subject using the variable type arm of which the length and rotation angle of joints, etc. are variable.

14 Claims, 17 Drawing Sheets

(30) Foreign Application Priority Data

Oct. 28, 2014 (KR) ........................ 10-2014-0147396
Oct. 28, 2014 (KR) ........................ 10-2014-0147422

(58) Field of Classification Search
USPC .................................. 378/62, 122, 196–198
See application file for complete search history.

(56) References Cited

U.S. PATENT DOCUMENTS

| | | | |
|---|---|---|---|
| 4,166,602 A * | 9/1979 | Nilsen | A61B 6/447 248/280.11 |
| 4,176,278 A * | 11/1979 | Cushman | A61B 6/145 378/119 |
| 4,259,583 A | 3/1981 | Albert | |
| 4,356,400 A | 10/1982 | Polizzi et al. | |
| 4,426,716 A * | 1/1984 | Muether | A61B 6/4429 378/197 |
| 4,503,552 A * | 3/1985 | Miyahara | A61B 6/4429 378/196 |
| 4,993,057 A * | 2/1991 | Runnells | A61B 6/4429 378/193 |
| 5,048,070 A * | 9/1991 | Maehama | A61B 6/4464 378/10 |
| 5,113,424 A * | 5/1992 | Burdea | A61B 6/08 378/168 |
| 5,475,730 A * | 12/1995 | Galando | A61B 6/4405 378/157 |
| 5,631,943 A * | 5/1997 | Miles | A61B 6/145 378/102 |
| 5,781,610 A | 7/1998 | Miles | |
| 6,038,287 A | 3/2000 | Miles | |
| 6,155,713 A * | 12/2000 | Watanabe | A61B 6/4441 378/197 |
| 6,200,024 B1 * | 3/2001 | Negrelli | A61B 6/4233 378/196 |
| 6,435,715 B1 * | 8/2002 | Betz | A61B 6/4458 378/197 |
| 6,496,558 B2 * | 12/2002 | Graumann | A61B 6/0478 378/197 |
| 6,543,936 B2 * | 4/2003 | Feldman | A61B 6/145 378/191 |
| 6,553,096 B1 * | 4/2003 | Zhou | A61B 6/4028 378/122 |
| 6,582,121 B2 * | 6/2003 | Crain | A61B 6/107 378/189 |
| 6,592,259 B2 * | 7/2003 | Crain | A61B 6/107 378/196 |
| 6,661,875 B2 * | 12/2003 | Greenwald | H01J 35/025 378/119 |
| 6,733,176 B2 * | 5/2004 | Schmitt | A61B 6/4464 378/196 |
| 6,826,254 B2 * | 11/2004 | Mihara | A61N 5/10 250/492.3 |
| 6,851,853 B2 * | 2/2005 | Nakagawa | A61B 6/4405 378/197 |
| 6,857,609 B2 * | 2/2005 | Stoianovici | F16M 11/12 248/276.1 |
| 6,935,779 B2 * | 8/2005 | Zhang | A61B 6/08 378/196 |
| 7,029,176 B2 * | 4/2006 | Martti | A61B 6/145 378/197 |
| 7,048,439 B2 * | 5/2006 | Hubner | A61B 6/105 248/288.51 |
| 7,073,939 B2 * | 7/2006 | Spahn | A61B 6/488 378/189 |
| 7,090,396 B2 * | 8/2006 | Boomgaarden | A61B 6/4464 378/196 |
| 7,175,345 B2 * | 2/2007 | Kantor | H05G 1/04 378/197 |
| 7,182,511 B2 * | 2/2007 | Boomgaarden | A61B 6/4464 378/197 |
| 7,401,977 B2 * | 7/2008 | Graumann | A61B 6/4441 378/197 |
| 7,429,130 B2 * | 9/2008 | Malucelli | A61B 6/14 378/197 |
| 7,441,953 B2 * | 10/2008 | Banks | A61B 5/1038 378/197 |
| 7,448,800 B2 * | 11/2008 | Steger | A61B 6/4464 248/317 |
| 7,452,130 B2 * | 11/2008 | Molz | A61B 6/4464 378/101 |
| 7,500,784 B2 * | 3/2009 | Grebner | A61B 6/4441 378/193 |
| 7,530,739 B2 * | 5/2009 | Lurz | A61B 6/4441 378/197 |
| 7,596,205 B2 * | 9/2009 | Zhang | A61B 6/032 378/196 |
| 7,628,537 B2 * | 12/2009 | Schulze-Ganzlin | A61B 6/145 378/170 |
| 7,806,589 B2 * | 10/2010 | Tashman | A61B 5/1038 378/193 |
| 7,832,927 B2 * | 11/2010 | Dyreby | A61B 6/587 378/194 |
| 7,905,658 B2 * | 3/2011 | Gro(Eszett) | A61B 6/4458 378/193 |
| 7,938,579 B2 * | 5/2011 | Gro(Eszett) | A61B 6/4458 378/197 |
| 7,978,817 B2 * | 7/2011 | Rietzel | A61N 5/1049 378/197 |
| 7,988,357 B2 * | 8/2011 | Hornung | A61B 6/4233 378/197 |
| 8,201,999 B2 * | 6/2012 | Uchida | A61B 6/547 378/197 |
| 8,459,867 B2 * | 6/2013 | Muller | A61B 6/4464 378/196 |
| 8,534,915 B2 * | 9/2013 | Maschke | A61B 6/4411 378/196 |
| 8,534,916 B2 * | 9/2013 | Maschke | A61B 6/4014 378/197 |
| 8,606,348 B2 * | 12/2013 | Maschke | A61B 6/505 600/425 |
| 8,655,429 B2 * | 2/2014 | Kuduvalli | A61N 5/1049 600/407 |
| 8,757,876 B2 * | 6/2014 | Nakamura | A61B 6/0414 378/189 |
| 9,055,911 B2 * | 6/2015 | Sakuragi | A61B 6/4429 |
| 9,107,633 B2 * | 8/2015 | Muller | A61B 6/0407 |
| 9,326,747 B2 * | 5/2016 | Omura | A61B 6/4405 |
| 9,433,395 B2 * | 9/2016 | Kang | A61B 6/544 |
| 9,492,137 B2 * | 11/2016 | Iwamoto | A61B 6/4283 |
| 9,521,984 B2 * | 12/2016 | Moreno Vallejo | A61B 6/4405 |
| 9,554,768 B2 * | 1/2017 | Kim | A61B 6/4405 |
| 9,693,746 B2 * | 7/2017 | Ancar | A61B 6/08 |
| 9,833,215 B2 * | 12/2017 | Stopp | A61B 6/4452 |
| 9,861,328 B2 * | 1/2018 | Kang | A61B 6/4452 |
| 2002/0154742 A1 | 10/2002 | Feldman | |
| 2003/0210765 A1 | 11/2003 | Greenwald et al. | |
| 2004/0149874 A1 | 8/2004 | Stoianovici et al. | |

FOREIGN PATENT DOCUMENTS

| | | |
|---|---|---|
| KR | 20-2009-0000444 U | 1/2009 |
| KR | 10-2012-0097564 A | 9/2012 |

* cited by examiner

X-RAY PHOTOGRAPHING DEVICE COMPRISING VARIABLE TYPE ARM

CROSS REFERENCE TO RELATED APPLICATIONS

This application is a National Stage Patent Application of PCT International Patent Application No. PCT/KR2015/000761 (filed on Jan. 23, 2015) under 35 U.S.C. § 371, which claims priority to Korean Patent Application Nos. 10-2014-0008568 (filed on Jan. 23, 2014), 10-2014-0008507 (filed on Jan. 23, 2014), 10-2014-0147422 (filed on Oct. 28, 2014) and 10-2014-0147396 (filed on Oct. 28, 2014), the teachings of which are incorporated herein in their entireties by reference.

TECHNICAL FIELD

The present invention relates to an X-ray radiography device and, more particularly, to an X-ray radiography device having a variable arm that can radiate X-rays to a subject without limitations on position or direction, using a variable arm that can change in length and rotational angle of joints.

BACKGROUND ART

An X-ray radiography device obtains a radiograph by radiating a predetermined amount of X-rays, which are generated by an X-ray generator, to a predetermined portion of a body to be radiographed, sensing the amount of X-ray passing through the portion by means of an X-ray sensing unit, and calculating X-ray absorption ratios of predetermined points in the portion of the body. In the X-ray radiography device, the X-ray generator needs be easily changed in position and direction to face desired portions of a subject and the position and direction need to be fixed while an X-ray is generated after they are determined.

FIG. 1 shows an X-ray radiography device having a plurality of arms in the related art. The X-ray radiography device 10 of the related art, as shown in FIG. 1, includes a body 11 that is fixed to a wall or other equipment and an X-ray generator 12 that radiates an X-ray to a subject, in which they are connected through an arm assembly 20 having a plurality of joints. A power supply and a control panel are disposed at the body 11, while an X-ray emitter and a collimator are disposed at the X-ray generator 12. An X-ray sensing unit (not shown) may be provided inside or outside a subject that the X-ray generator 12 faces.

The arm assembly 20 is formed by connecting a plurality of unit arms 21, 22, 23, and 24. Adjacent unit arms 21, 22, 23, and 24 are connected by various joints so that they can rotate about rotational shafts a1~a7, respectively, within the range of 0 to 180 degrees. The unit arms 21, 22, 23, and 24 and the joints function as paths for a power supply line and signal lines connecting the body 11 and the X-ray generator 12.

In order to perform radiography using the X-ray radiography device 10, for example, for dental examination and treatment, a user puts the X-ray sensing unit, which is called an intraoral X-ray sensor, inside the mouth of a patient and has to operate the arm assembly 20 so that the X-ray generator 12 faces the X-ray sensing unit. In particular, patients have different sizes, so the user has to appropriately configure the X-ray generator every time toward the desired portions to radiograph of the patient. However, it is difficult to control the position and direction of the X-ray generator 12 by operating the arm assembly 20. This is because it is required to consider the lengths of the unit arms 21, 22, 23, and 24 of the arm assembly 20 and the rotational characteristics of the joints should avoid interference with the body of a patient. Further, considering the weight of only the X-ray generator 12 is around 10 kg, it is hard for a user to move the arm assembly 20 supporting the arm.

Further, in terms of manufacturing the device, the structure is complicated due to the plurality of unit arms and joints, and the manufacturing cost and the percent defective are easily increased and the reliability is easily deteriorated in proportion to the number of the parts.

DETAILED DESCRIPTION OF THE INVENTION

Technical Problem

The present invention has been made in an effort to solve the problems and an object of the present invention is to provide an X-ray radiography device that has a variable arm that enables a user to easily move and turn an X-ray generator, has a high degree of freedom in motion, and has a simple structure.

Technical Solution

In order to achieve the object, the present invention provides an X-ray radiography device that includes: a radiographing body including an X-ray generator; and a variable arm relatively changing a position and a direction of the radiographing body with respect to a temporarily fixed position, in which the variable arm includes: a variable connection member configured to change in length or direction by an external force; a fixed end configured to be an end of the variable connection member and fixed at at least the temporarily fixed position; and a free end configured to be an opposite end to the fixed end, be connected to the radiographing body, and to be changed in position and direction relative to the fixed end with transformation of the variable connection member. The fact that the fixed end is at least temporarily fixed means that an object to which the fixed end is fixed may be a permanently fixed structure such as a wall, or that the fixed end is fixed to other equipment, furniture, or an object that can move but maintains a fixed position during radiography such that a patient can be radiographed.

In an embodiment, the variable connection member may be a variable corrugated pipe that being partially freely changeable by the external force and may have a space through which a cable passes.

In an embodiment, the variable corrugated pipe may include a plurality of gooseneck arms having different thicknesses and being connected to each other.

In an embodiment, the gooseneck arms may include: a first gooseneck arm reinforced by a first reinforcing layer, which is made of a metal or a synthetic resin having a first thickness (t1) (t1>0) on an inner side thereof; and a second gooseneck arm reinforced with a second reinforcing layer made of the metal or the synthetic resin having a second thickness (t2) (t1>t2>0) on an inner side thereof.

In an embodiment, flexibility of the variable connection member may increase along a direction from the fixed end to the free end.

In an embodiment, the variable connection member may be a multi-stepped arm including multi-stepped pipes having different diameters to be stretched or contracted for a length adjustment.

In an embodiment, the X-ray radiography device may further include a fixed body connected to the fixed end, to be fixed to an external structure, and having a power supply therein, and a cable connecting the fixed body and the radiographing body to each other and connected through an inside space of the variable connection member.

In an embodiment, the free end may be separable from the radiographing body, the fixed end may be separable from the fixed body, and the variable connection member may be longitudinally partially open or cut to take out the cable.

In an embodiment, when the variable connection member is separated from the cable, the cable may be put into the fixed body.

In an embodiment, the X-ray radiography device may further include a cable exit disposed at the fixed end to take out a cable inserted in the variable connection member.

In an embodiment, the X-ray radiography device may further include a clamp connected to the fixed end and to be fixed to an external structure.

In an embodiment, the X-ray radiography device may further include a body support connected to the fixed end and placed on a portion of a body of a patient who is a subject to be radiographed.

In an embodiment, the body support may be a shoulder support or a headrest.

In an embodiment, the X-ray generator may include a field emission type of electron emitter using a nano-scaled emitter.

In an embodiment, the radiographing body may be detachably or rotatably connected to the variable arm.

Advantageous Effects

According to the present invention, it is possible to provide an X-ray radiography device that enables a user to easily move and turn an X-ray generator, has a high degree of freedom in motion, and has a simple structure.

Therefore, it is possible to provide a product that can be very conveniently used by a user, to improve reliability and reduce the manufacturing cost by simplifying the structure, and to improve mobility by reducing the weight of the X-ray radiography device.

BEST MODE FOR CARRYING OUT THE INVENTION

Hereinafter, embodiments of the present invention will be described with reference to the accompanying drawings. The following embodiments may be modified in various ways and the range of the present invention is not limited to the following embodiments. Embodiments of the present invention are provided to clearly give the technical spirit of the present invention to those skilled in the art.

Figure 1:
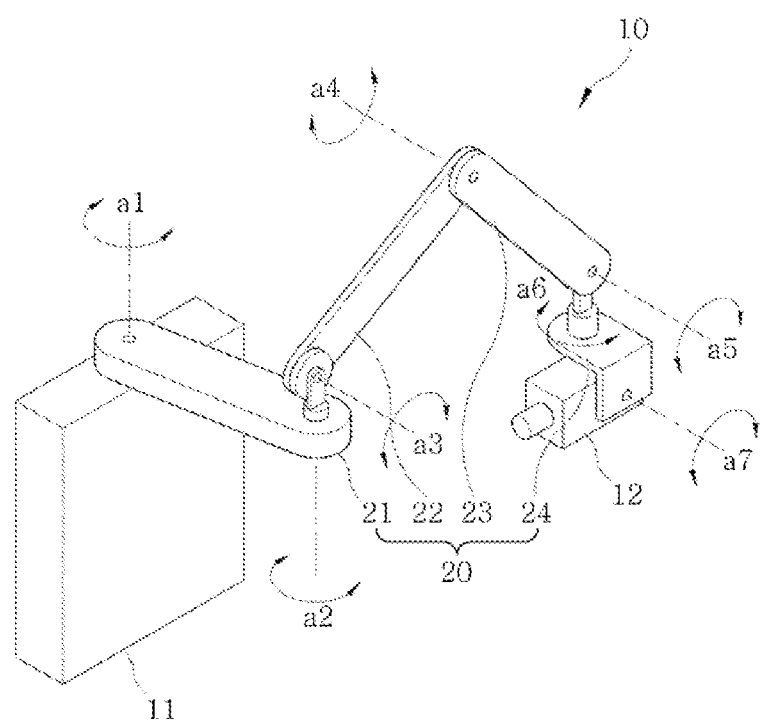
FIG. 1 shows an X-ray radiography device having a plurality of arms in the related art.
Figure 2:
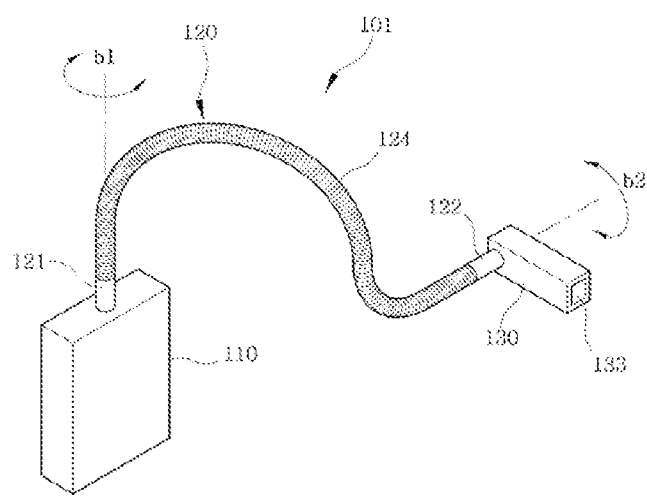
FIG. 2 is a view showing an X-ray radiography device according to a first embodiment of the present invention.

FIG. 2 is a view showing an X-ray radiography device according to a first embodiment of the present invention. An X-ray radiography device 101 according to this embodiment includes a radiographic variable arm 120, a fixed body 110, and a radiographing body 130. The fixed body 110 is fixed to an external structure such as a wall or other equipment and includes a power supply therein. The radiographic variable arm 120 has: a variable connection member 124 that is a variable corrugated pipe having a predetermined length and being freely partially changeable by external force and provides a space therein through which a cable can pass; a fixed end 121 that is one end of the variable connection member 124 and fixed to the fixed body 110, and a free end 122 that is an opposite end to the fixed end 121 of the variable connection member 124 and is changed in position and direction relative to the fixed end 121 with transformation of the variable connection member 124. The free end 122 is connected to the radiographing body 130. The fixed end 121 may rotate about an axis b1 with respect to the fixed body 110 and the free end 122 may rotate about an axis b2 with respect to the radiographing body 130.

A variable corrugated pipe made of metal such as stainless steel may be used for the variable connection member 124. When force over a predetermined level is applied perpendicularly to the longitudinal direction of the variable connection member 124, the portion receiving the force is transformed, or when a force is not applied or a force less than a predetermined level is applied, the variable connection member 124 maintains the shape. Accordingly, a variable corrugated pipe that is transformed by force applied transversely (perpendicularly to the longitudinal direction) over a predetermined level larger than the weight of the radiographing body 130 may be used for the variable connection member 124. As long as satisfying this condition, the part used for a microphone stand may be used, for example.

In this embodiment, the fixed end 121 and the free end 122 are short pipes without wrinkles coupled to both ends of the variable connection member 124. This structure is advantageous in connection to the fixed body 110 and the radiographing body 130. However, the present invention is not limited to this structure. The fixed end 121 and the free end 122 may be not separate members, but both end portions of the variable connection member 123.

The radiographic variable arm 120 composed of the variable connection member 124, the fixed end 121, and the free end 122 provides a passage through which a cable can be connected from the fixed end 121 to the free end 122. The fixed body 110 is connected to an external power supply terminal or may have a power supply including a battery, whereby power can be supplied to the radiographing body 130 through the cable. Further, a control panel that can control the X-ray generator in the radiographing body 130 may be disposed in the fixed body 110, in which a cable for transmitting control signals may be connected through the radiographic variable arm 120.

The radiographing body 130 includes an X-ray generator at a portion thereof and may further include a collimator 133 that controls the radiation range of an X-ray from the X-ray generator. In the X-ray radiography device 101 according to this embodiment, it is advantageous that the radiographing body 130 is light, and the weight may be within about 1 kg. To this end, the X-ray generator may be equipped with a field emission type of electron emitter, which uses a nanostructure material such as a carbon nanotube, and an X-ray target.

MODE FOR INVENTION

Figure 3:
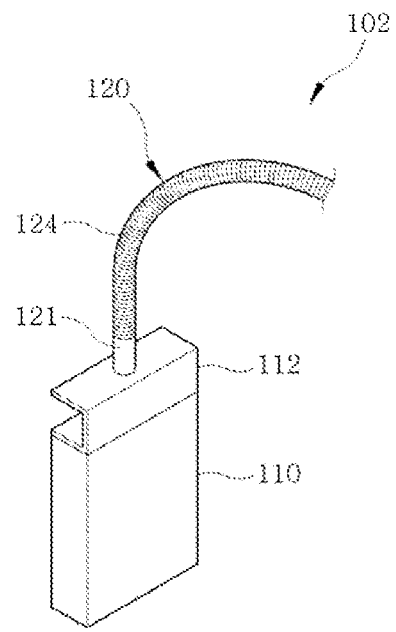
FIG. 3 is a view showing an X-ray radiography device according to a second embodiment of the present invention.

FIG. 3 is a view showing an X-ray radiography device according to a second embodiment of the present invention. An X-ray radiography device 102 according to this embodiment may further include a clamp 112 that is coupled to the fixed end 121 of the radioscopic variable arm 120 to be fixed to an external structure, in addition to the configuration of the X-ray radiography device 101 according to the first embodiment. The clamp 112 may be coupled in advance to the fixed body 110 of the X-ray radiography device 102. The clamp 112 may be fixed in various ways, for example, by screws or elastic members such as forceps. Other configurations of the X-ray radiography device 102 according to this embodiment are the same as that of the X-ray radiography device 101 according to the first embodiment.

Figure 4:
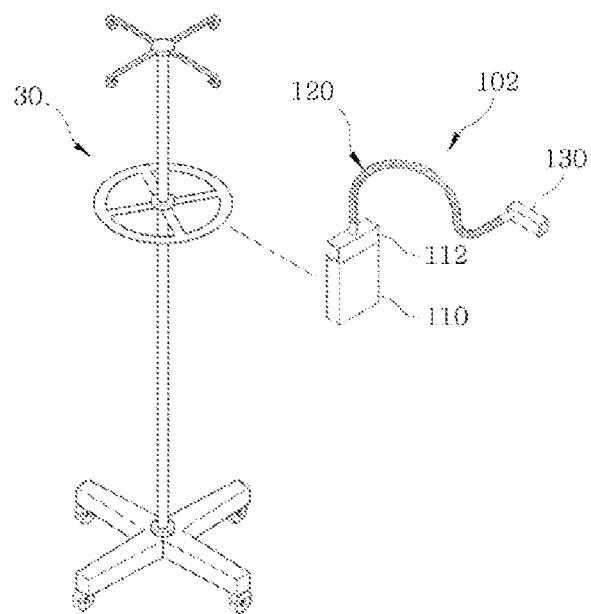
FIG. 4 is a view showing an example of using the X-ray radiography device according to the embodiment shown in FIG. 3.

FIG. 4 is a view showing an example of using the X-ray radiography device according to the embodiment shown in FIG. 3. The X-ray radiography device 102 according to this embodiment may be fixed for use to a common movable stand 30 that is generally used for holding the containers of ringer's solution. Although the clamp 112 is held on the handle of the movable stand 30 in this embodiment, it may be fixed to the bar of the stand.

Figure 5:
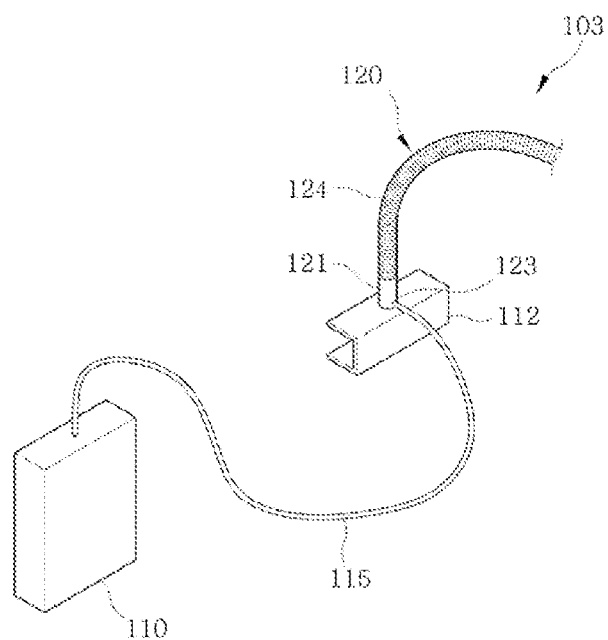
FIG. 5 is a view showing an X-ray radiography device according to a third embodiment of the present invention.

FIG. 5 is a view showing an X-ray radiography device according to a third embodiment of the present invention. An X-ray radiography device 103 according to this embodiment further includes, in addition to the configuration of the X-ray radiography device 101 according to the first embodiment, a clamp 112 that is coupled to the fixed end 121 of the radiographic variable arm 120 to be fixed to an external structure, as in the second embodiment, and further includes a cable exit 123 disposed at the fixed end 121 of the variable arm 120 to take out a cable 115 inserted in the variable arm 120. The cable 115 may be connected to the fixed body 110 separated from the radiographic variable arm 120. Other configurations of the X-ray radiography device 103 according to this embodiment are the same as that of the X-ray radiography device 101 according to the first embodiment.

Figure 6:
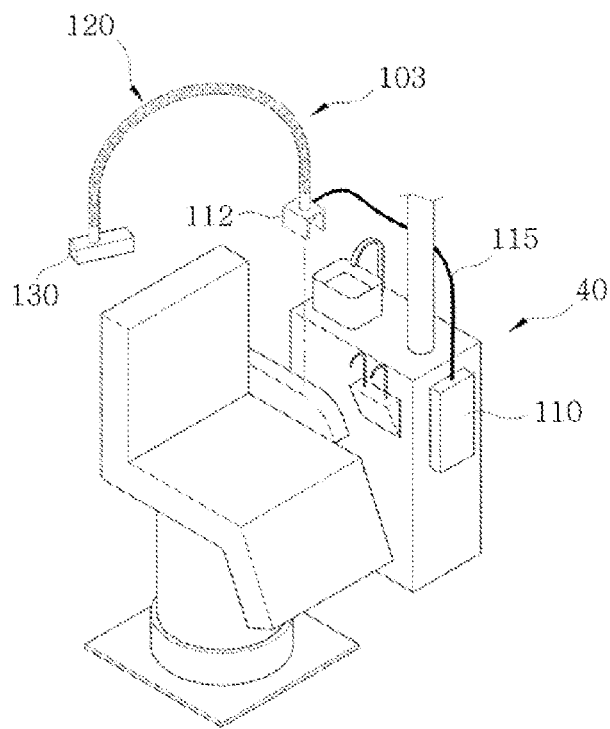
FIG. 6 is a view showing an example of using the X-ray radiography device according to the embodiment shown in FIG. 5.

FIG. 6 is a view showing an example of using the X-ray radiography device according to the embodiment shown in FIG. 5. The X-ray radiography device 102 according to this embodiment may be fixed for use to a dental unit chair 40 that is generally used in dental clinics. Although the clamp 112 is disposed on an armrest 41 of the dental unit chair 40 in this embodiment, it may be fixed to other portions. Further, the fixed body 110 may be separated from the radiographic variable arm 120 and installed at a fixed structure such as a shelf of the dental unit chair 40 and may be connected through the cable 115 coming out of the cable exit.

Figure 7:
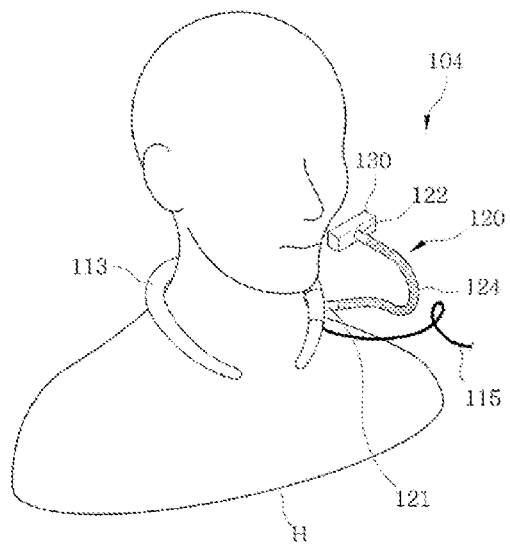
FIG. 7 is a view showing an X-ray radiography device according to a fourth embodiment of the present invention.
Figure 8:
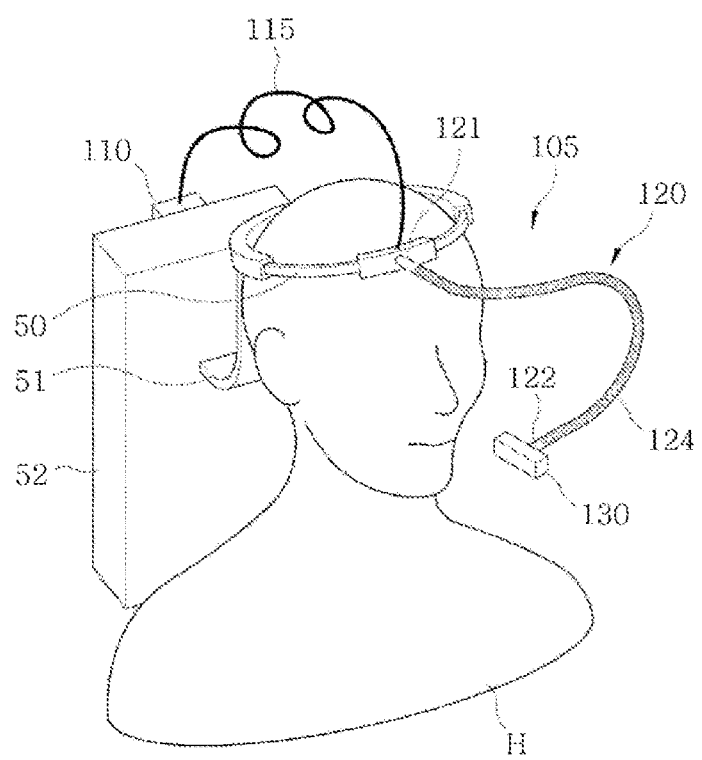
FIG. 8 is a view showing an X-ray radiography device according to a fifth embodiment of the present invention.

FIG. 7 is a view showing an example of using the X-ray radiography device according to a fourth embodiment and FIG. 8 is a view showing an example of using an X-ray radiography device according to a fifth embodiment. X-ray radiography devices 104 and 105 according to the fourth and fifth embodiments may further include a body support that is connected to the fixed end 121 of the radiographic variable arm 120 and is placed on a portion of the body of a patient H who is the subject to be radiographed. In the X-ray radiography device 104 according to the fourth embodiment, a shoulder support 113, which is placed on the shoulders of the patient H as an example of the body support, is connected to the fixed end 121 of the radiographic variable arm 120. In the X-ray radiography device 105 according to the fifth embodiment, a headrest 50, which is placed on the head of the patient H as another example of the body support, is connected to the fixed end 121 of the radiographic variable arm 120. The headrest 50, which is a part connected to the dental treatment equipment 52 in the related art, may be the part included in the dental treatment equipment 52 in the related art. The cable 115 taken out of the radiographic variable arm 120 may be connected to the fixed body 110 that is separately installed.

Figure 9:
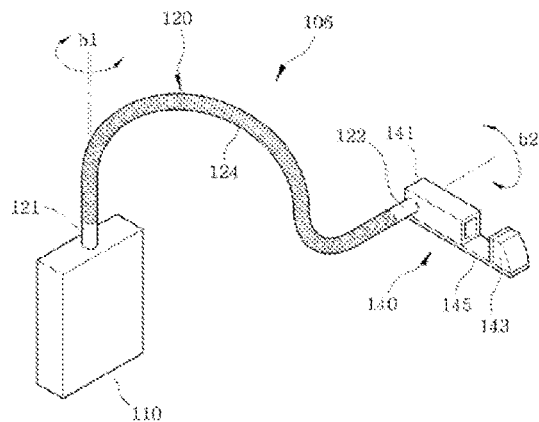
FIG. 9 is a view showing an X-ray radiography device according to a sixth embodiment of the present invention.
Figure 10:
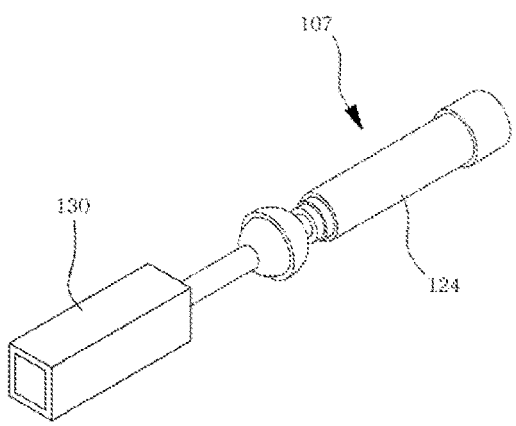
FIGS. 10 to 13 are views showing an X-ray radiography device according to a seventh embodiment of the present invention.
Figure 11:
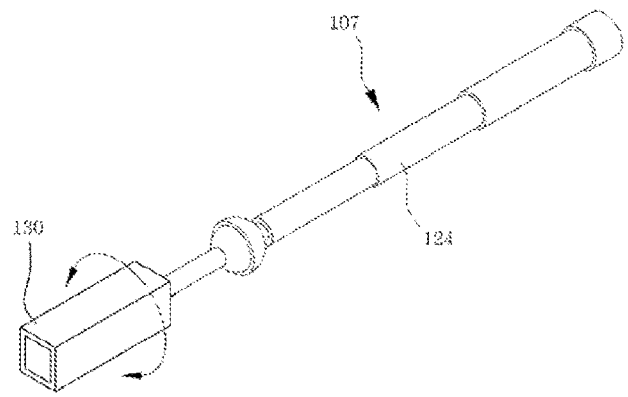
Figure 12:
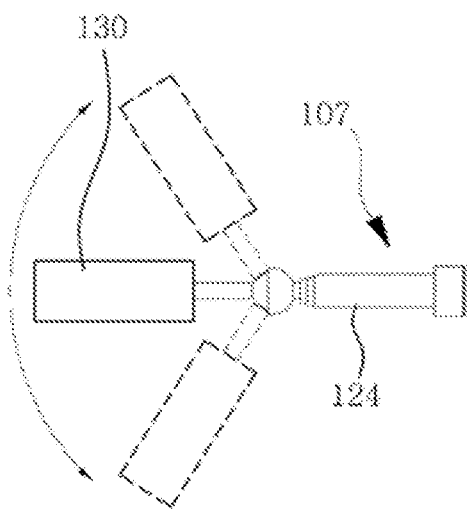
Figure 13:
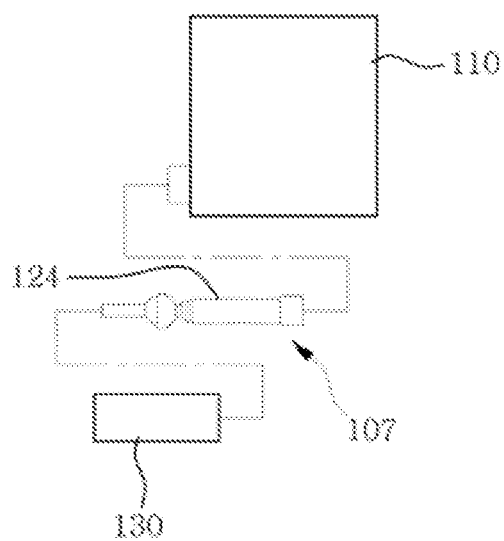

FIG. 9 is a view showing an X-ray radiography device according to a sixth embodiment of the present invention. An X-ray radiography device 16 according to this embodiment is the same as the X-ray radiography device 101 according to the first embodiment in terms of the radiographic variable arm 120, but is different in the configuration of a radiographing body 140. In this embodiment, the radiographing body 140 may further include a first body 143 in which any one of an X-ray generator and an X-ray sensing unit is disposed, a second body 141 in which the other one of the X-ray generator and the X-ray sensing unit is disposed, and a connection frame 145 connecting the first and second bodies. The positions of the X-ray generator 141 and the X-ray sensing unit 143 may be exchanged on the connection frame 145.

It is advantageous for the radiographing body 140 be light and the weight may be within about 1 kg. To this end, the X-ray generator may be equipped with a light electron emitter such as a field emission type of electron emitter, which uses a carbon nanotube, and an X-ray target.

The radiographing body 140 of the X-ray radiography device 106 according to this embodiment will be described in a corresponding part below.

The X-ray radiography devices 101 to 106 according to the embodiments may be modified in various ways, that is, for example, the cable for supplying power to the radiographing bodies 140 and 130 may be connected to the fixed body 110 not through the inside of the radiographic radio corrugated arm 120 or may be connected to the power supply of existing equipment or a movable battery pack. When a power circuit is disposed in the radiographing bodies 140 and 130, it may be connected directly to an external power terminal. Further, the radiographing bodies 140 and 130 may be separably connected to the free end 122 of the radiographic variable corrugated arm 120, and when they are separated, the cable 115 may extend out of the variable connection member 124. To this end, the cable 115 may be elastically wound in the radiographic variable corrugated arm 120 or the fixed body 110 to be pulled out when the radiographing bodies 140 and 130 are pulled away from the free end 122.

FIGS. 10 to 13 are views showing an X-ray radiography device according to a seventh embodiment of the present invention. In an X-ray radiography device 107 according to this embodiment, a variable connection member 124 may be a multi-stepped arm including multi-stepped pipes, and the other configuration is the same as that of the X-ray radiography device 101 according to the first embodiment.

Further, the X-ray radiography device 107 according to the seventh embodiment can be changed in length, but is limited in control of the angle of the radiographing body 130, as compared with the X-ray radiography device 101 according to the first embodiment.

Accordingly, a semispherical portion with an empty internal space may be formed at an end of the variable connection member 124 and a coupling ball may be formed at the radiographing body 130 so that the variable connection member 124 can tilt with them coupled.

Further, the variable connection member 124 and the radiographing body 130, and the variable connection member 124 and the fixed body 110 may be detachably or rotatably combined in well-known types, for example, by thread-fastening or fitting, and terminals may be disposed therein and coupled to each other to supply power or transmit predetermined control signals.

Further, though not shown, a cable reel for winding or unwinding a cable may be disposed in the fixed body 110 so that the cable inside can be moved when the multi-stepped arm is stretched or contracted.

That is, it is possible to prevent damage to the cable inside even if the variable connection member 124 changes in length.

Figure 14:
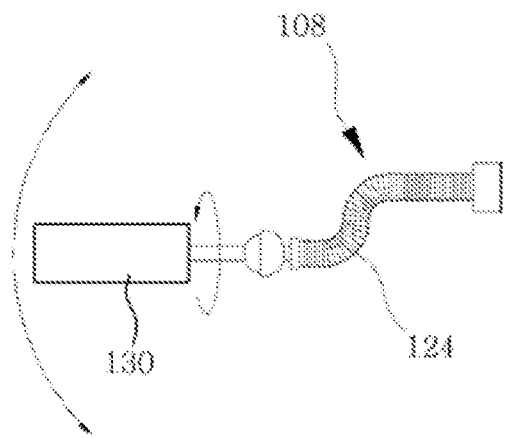
FIGS. 14 to 15 are views showing an X-ray radiography device according to an eighth embodiment of the present invention.
Figure 15:
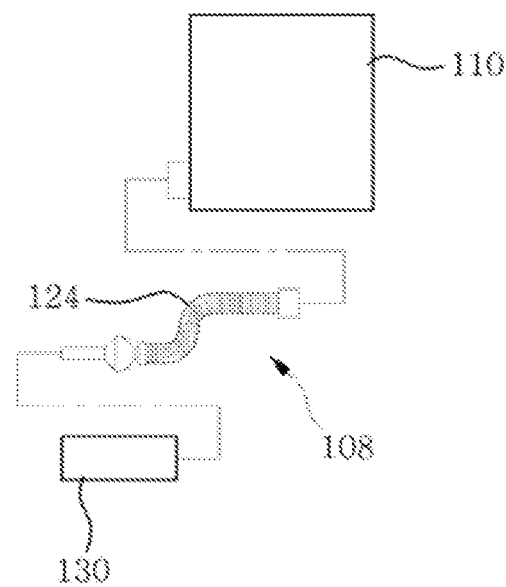

FIGS. 14 to 15 are views showing an X-ray radiography device according to an eighth embodiment of the present invention. In an X-ray radiography device 108 according to this embodiment, the variable connection member 124 is a variable corrugated pipe, and a semispherical portion with an empty inside is formed at an end of the variable connection member 124 and a coupling ball is formed at the radiographing body 130 so that the variable connection member 124 can tilt with free rotation with them coupled.

That is, this embodiment has the advantage that, as compared with the variable arm 120 according to the first embodiment, it is possible to more smoothly move the variable arm with a higher degree of freedom and there is little limitation in radiation position and angle of X-rays.

Figure 16:
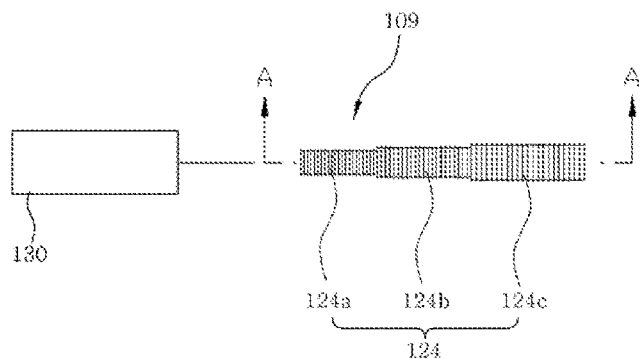
FIGS. 16 to 18 are views showing an X-ray radiography device according to a ninth embodiment of the present invention.
Figure 17:
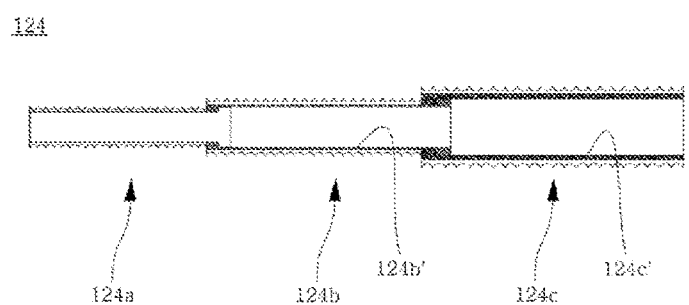
Figure 18:
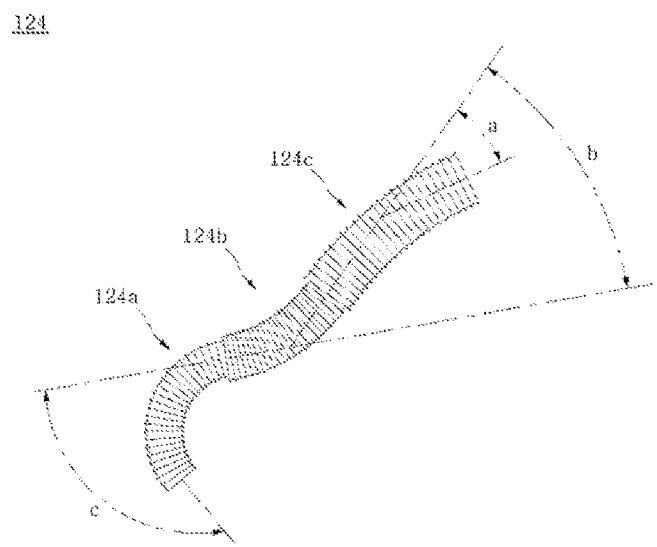

FIGS. 16 to 18 are views showing an X-ray radiography device according to a ninth embodiment of the present invention. In an X-ray radiography device 109 according to this embodiment, the variable connection member 124 is composed of a plurality of gooseneck arms 124a, 124b, and 124c, and the other configuration is substantially the same as the X-ray radiography device 101 according to the first embodiment.

The gooseneck arms 124a, 124b, and 124c may have different thicknesses.

In detail, the gooseneck arms 124a, 124b, and 124c may include a first gooseneck arm 124c that is thickest, a second gooseneck arm 124b that is secondarily thick, and a third gooseneck arm 124a that is thinnest.

FIG. 17 is a cross-sectional view taken along line A-A in FIG. 16, in which the first gooseneck arm 124c may be reinforced on the inner side by a first reinforcing layer 124c' made of metal or synthetic resin and having a predetermined thickness t1 and may be coupled to the fixed body 110 where it is supposed to bend less.

Next, a second reinforcing layer 124b' made of metal or synthetic resin and having a thickness t2 smaller than that of the first reinforcing layer 124c' of the first gooseneck 124c is disposed on the inner side of the second gooseneck arm 124b.

On the other hand, the third gooseneck arm 124a is not provided with a reinforcing layer therein in order to be bent well and coupled to the radiographing body 130.

In the gooseneck arms, the first reinforcing layer 124c' in the first gooseneck arm 124c is made of metal or synthetic resin with a first thickness t1 (t1>0) and the second reinforcing layer 124b' in the second gooseneck arm 124b is made of metal or synthetic resin with a thickness t2 (t1>t2>0).

Accordingly, as shown in FIG. 18, the first gooseneck arm 124c that is thickest bends at a smallest angle (a), the second gooseneck arm 124b that is secondarily thick bends at a medium angle (b), and the third gooseneck arm 124a that is thin and bends well bends at a largest angle (c) (a<b<c).

Figure 19:
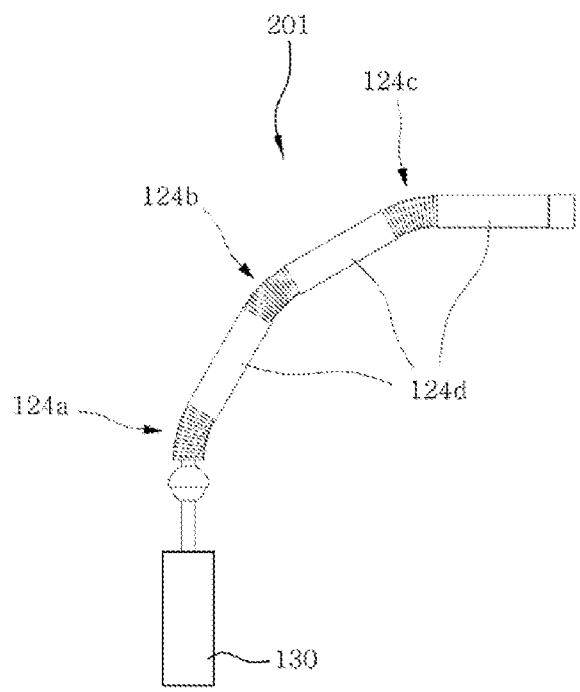
FIGS. 19 to 20 are views showing an X-ray radiography device according to a tenth embodiment of the present invention.
Figure 20:
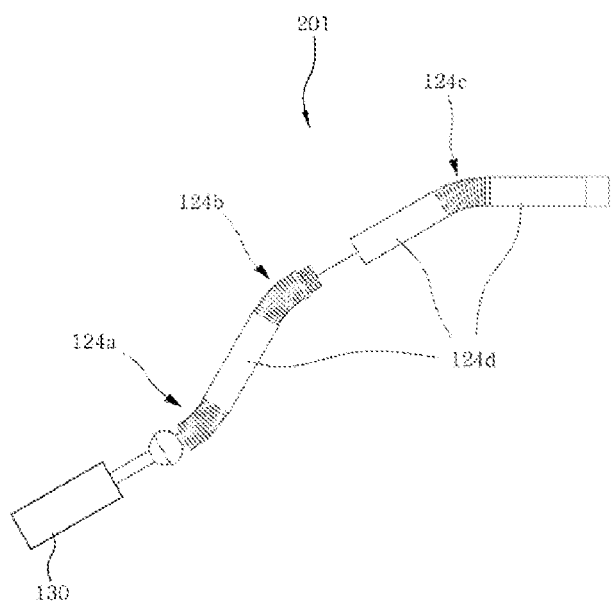

FIGS. 19 and 20 are views showing an X-ray radiography device according to a tenth embodiment of the present invention. In an X-ray radiography device 201 according to this embodiment, the variable connection member 124 is formed by combining a plurality of gooseneck arms 124a, 124b, and 124c and a specific pipe-shaped extension arm 124d between the gooseneck arms 124a, 124b, and 124c. The other configuration is substantially the same as the X-ray radiography device 109 according to the ninth embodiment.

Accordingly, the X-ray radiography device 201 according to this embodiment can have a larger degree of freedom in control of the length, as compared with the X-ray radiography device 109 according to the ninth embodiment.

Further, as in FIG. 20, it is possible to increase or decrease the length of the variable connection member by separating or combining the gooseneck arms 124a, 124b, and 124c and the extension arms 124d.

The variable connection member 124 may be composed of a smaller number of gooseneck arms and extension arms with a smaller length at the portion that is coupled to the fixed body 110 that is supposed to be less bent.

When the pipe-shaped extension arms 124d are made of PV, PE, PP, or PEEK that is an insulator, they are light and convenient to use, so the manufacturing cost can be reduced.

Accordingly, the portion close to the fixed body 110 is less bent in a stable state, so the entire radiographing body 130 is prevented from falling down. Further, the gooseneck arms sequentially have different flexibilities, so flexibility is given to the variable arm.

Figure 21:
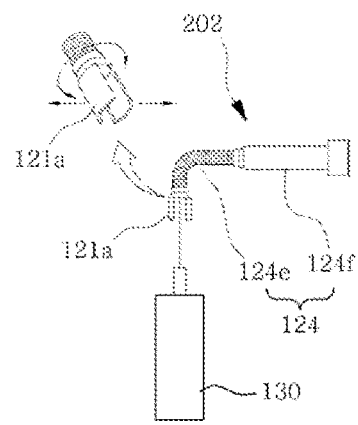
FIGS. 21 to 23 are views showing an X-ray radiography device according to an eleventh embodiment of the present invention.
Figure 22:
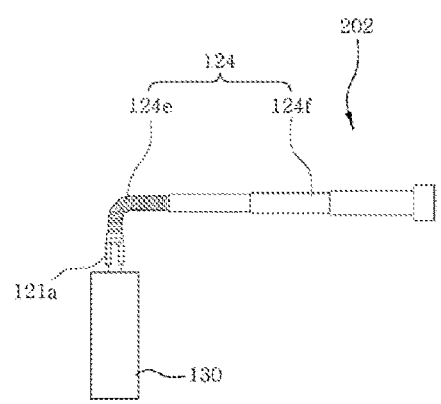
Figure 23:
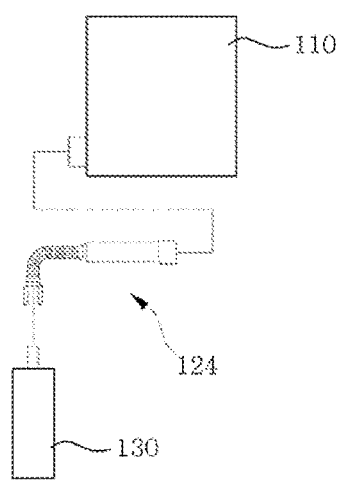

FIGS. 21 to 23 are views showing an X-ray radiography device according to an eleventh embodiment of the present invention. In an X-ray radiography device 202 according to this embodiment, the variable connection member 124 is formed by coupling a variable corrugated pipe 124e and a multi-stepped arm 124 to each other, and the variable corrugated pipe 124e and the radiographing body 130 are separably combined by a guide member 121a. The other configuration is substantially the same as the X-ray radiography device 101 according to the first embodiment.

That is, the X-ray radiography device 202 according to this embodiment can be controlled in length by the multi-stepped arm 124f and in angle by the variable corrugated pipe 124e.

Further, the X-ray radiography device 202 according to this embodiment has the advantage that the radiographing body 110 and the variable arm 124 can be easily coupled and separated by the guide member 121a.

Further, the guide member 121a prevents the coupled portion between the radiographing body 130 and the variable arm 124 from being bent or damaged, when being fastened, even if a user holds and moves the radiographing body 130, because the guide member 121a covers the coupled portion.

Figure 24:
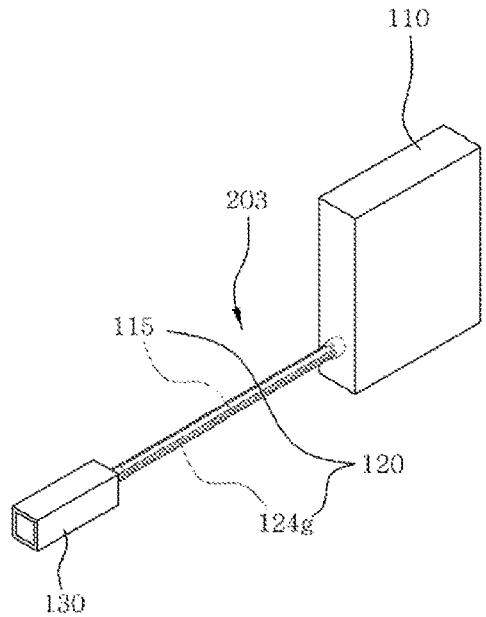
FIGS. 24 to 26 are views showing an X-ray radiography device according to a twelfth embodiment of the present invention.
Figure 25:
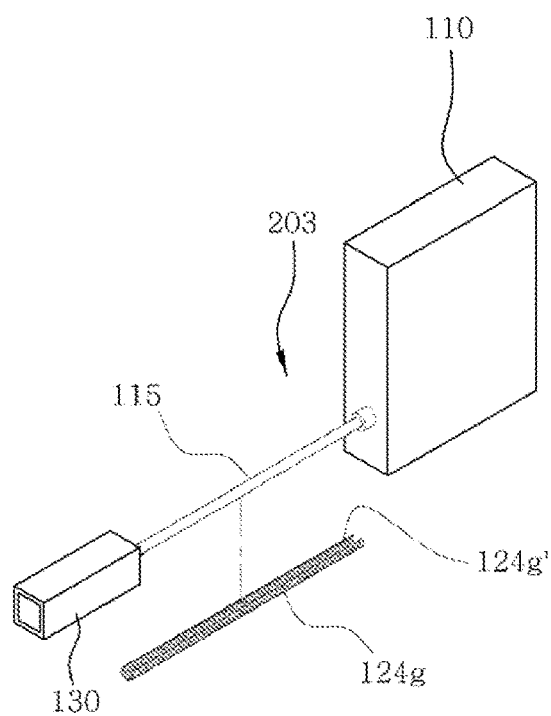
Figure 26:
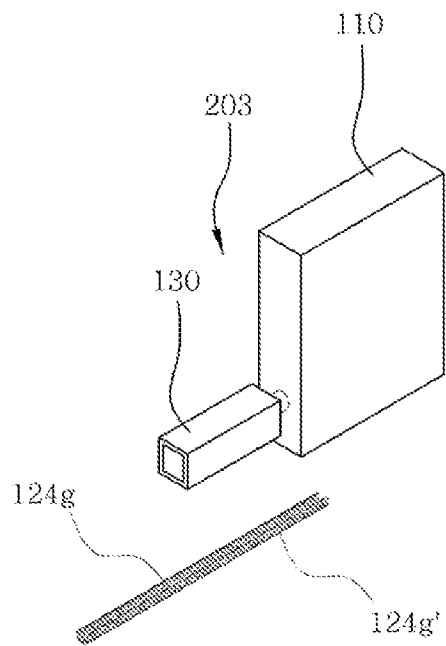
Figure 27:
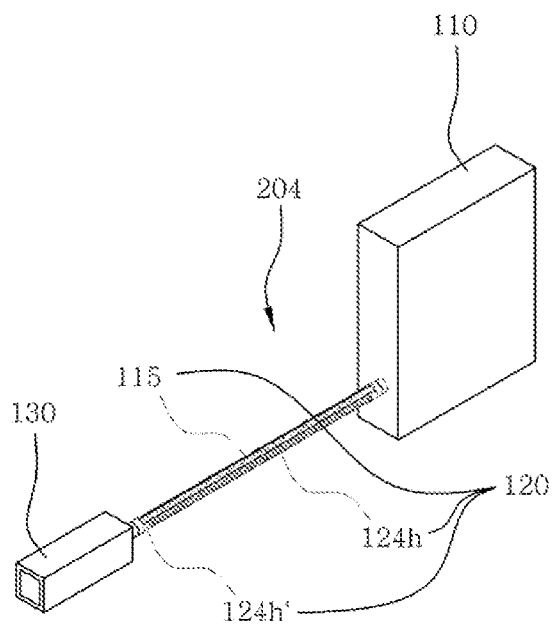
FIGS. 27 to 31 are views showing an X-ray radiography device according to thirteenth embodiment of the present invention.
Figure 28:
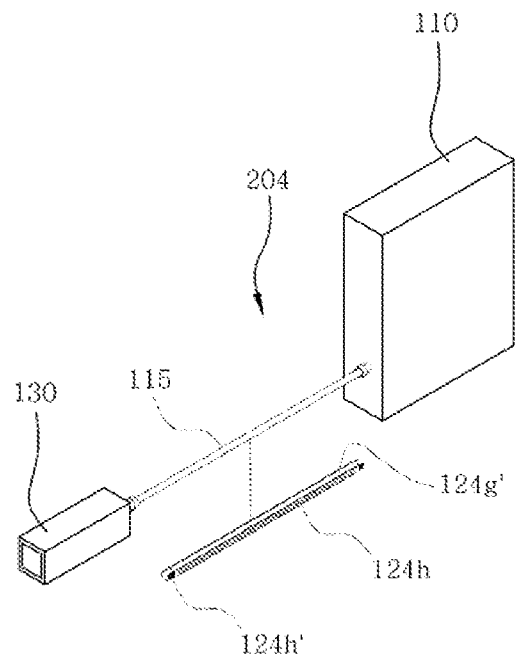
Figure 29:
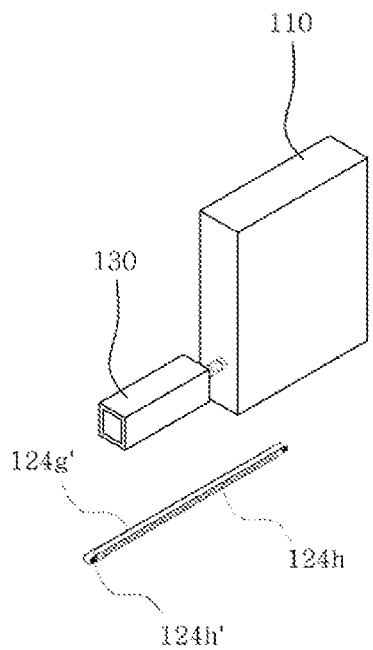

FIGS. 24 to 26 are views showing an X-ray radiography device according to a twelfth embodiment of the present invention. In an X-ray radiography device 203 according to this embodiment, a variable connection member 124 is a variable corrugated pipe 124g and the variable corrugated pipe 124g has a guide space 124g' formed by longitudinally opening or cutting a portion thereof.

The other configuration is the same as that of the X-ray radiography device 101 according to the first embodiment.

The guide space 124g' allows the variable corrugated pipe 124g to separate out from a cable 115 connecting the radiographing body 130 and the fixed body 110.

Further, a cable reel that can wind the cable 115 inside may be disposed in the fixed body 110.

That is, in order to use the X-ray radiography device 203 according to this embodiment, a user can take the cable 115 out of the fixed body 110 and fit the variable corrugated pipe 124g onto the cable 115. Further, after using, the user can separate the variable corrugated pipe 124g from the cable 115 and stow the cable 115 in the fixed body 110.

Accordingly, the X-ray radiography device 203 according to this embodiment has the advantage of being easily moved and kept.

FIGS. 27 to 31 are views showing an X-ray radiography device according to a thirteenth embodiment of the present invention. In an X-ray radiography device 204 according to this embodiment, a variable connection member 124 is a variable corrugated pipe 124h and a guide space 124g' is longitudinally formed in the variable corrugated pipe 124h, which is substantially the same as the twelfth embodiment.

However, the connectors 124h' for coupling the radiographing body 130 to the fixed body 110 are further disposed at both ends of the variable corrugated pipe 124h.

Figure 30:
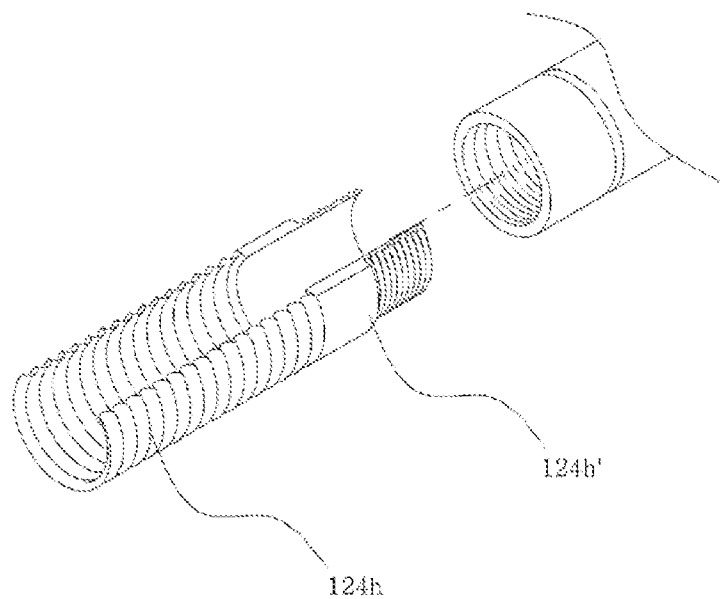
Figure 31:
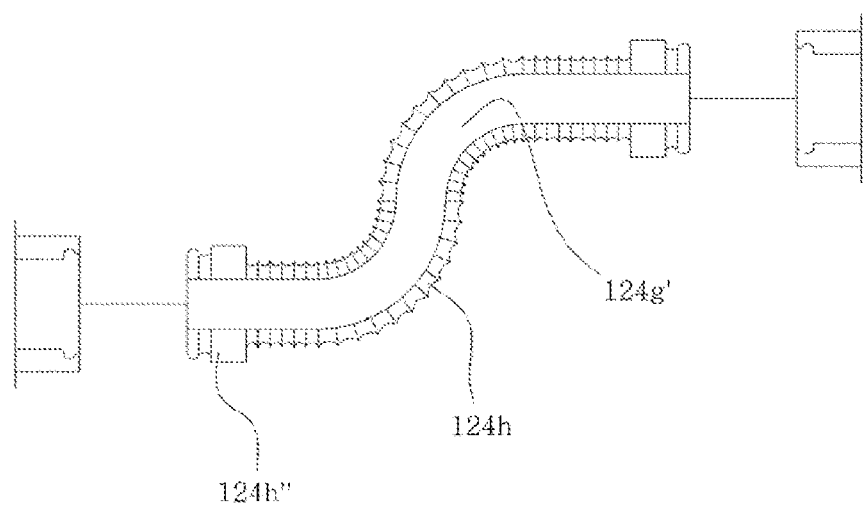

Further, the connectors 124h' may be threaded connectors 124h' to be thread-fastened, as shown in FIG. 30, or may be protruding connectors 124h" to be fitted, as shown in FIG. 31.

However, the connectors 124h' may be connectors that are coupled in various well-known types.

The protruding connectors 124h" may be connectors that can be elastically fitted. That is, after the variable corrugated pipe 124 is fitted on a cable 13 through the guide space 124g', the connector at a side of the variable corrugated pipe 124h is fitted into fastening hole of the fixed body 110 and the connector at the other side of the variable corrugated pipe 124h is fitted into a fastening hole of the radiographing body 130, thereby fitting is completed.

That is, the X-ray radiography device 204 according to this embodiment has the advantage that the variable corrugated pipe 124h can be stably coupled to the fixed body 110 and the radiographing body 130 in use, even if a user strongly handles the variable corrugated pipe 124h.

On the other hand, though not described above, FIGS. 32 to 37 show the radiographing body of the X-ray radiography device according to the embodiment of FIG. 9, and modified examples and using examples of the radiographing body.

Figure 32:
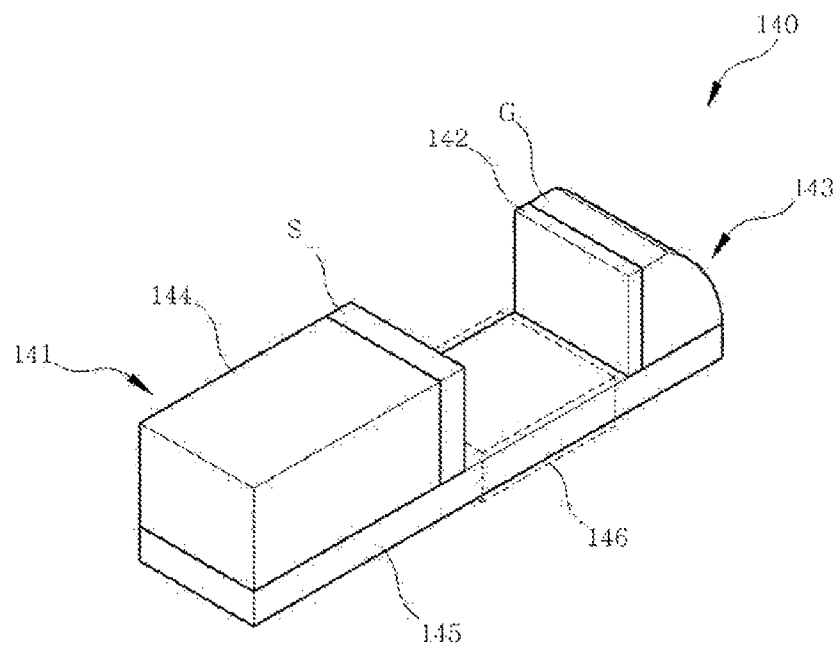
FIG. 32 is a view showing a radiographing body of the X-ray radiography device according to the ninth embodiment of the present invention.
Figure 33:
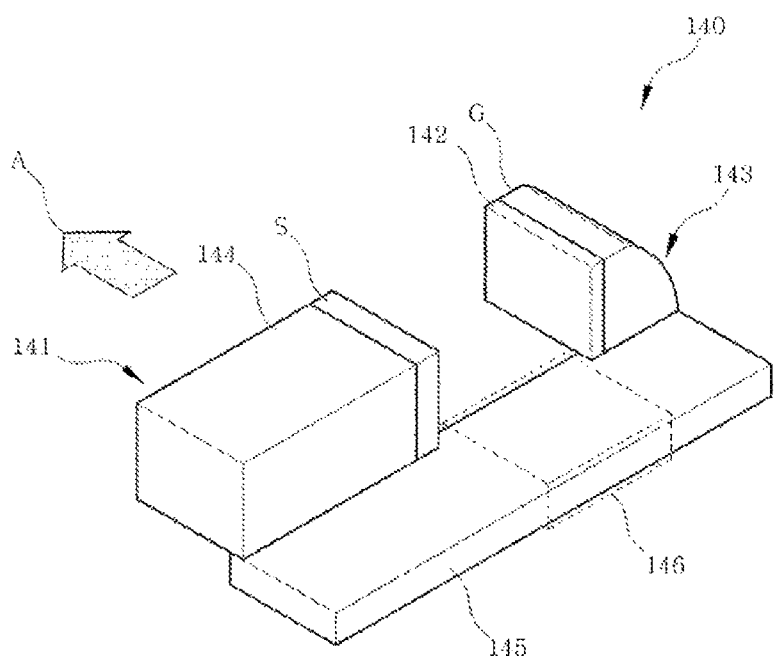
FIG. 33 is a view showing the radiographing body of FIG. 32 with first and second bodies moved.
Figure 34:
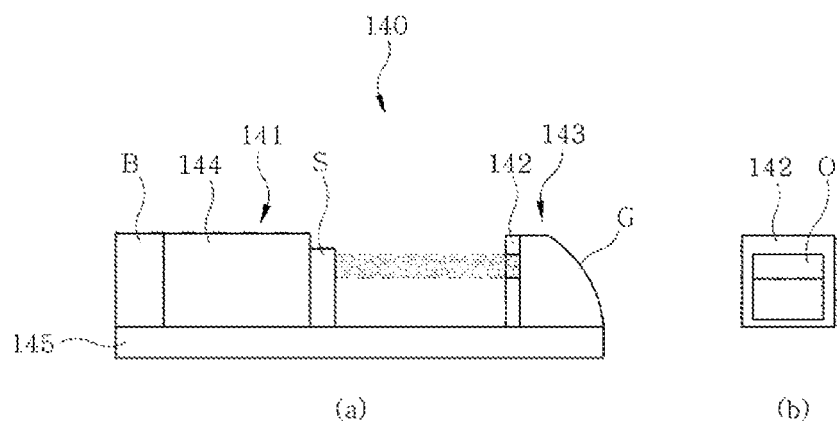
FIG. 34 is a view when an X-ray generator is mounted on the first body of the radiographing body of FIG. 32.
Figure 35:
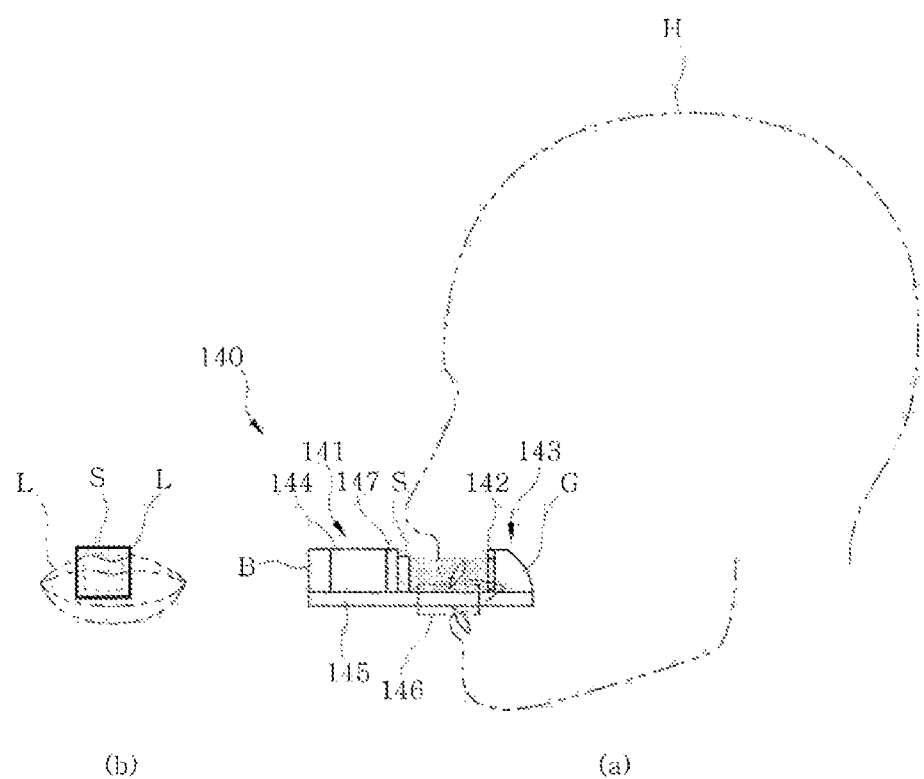
FIG. 35 is a view schematically showing radiography using the radiographing body of FIG. 34.
Figure 36:
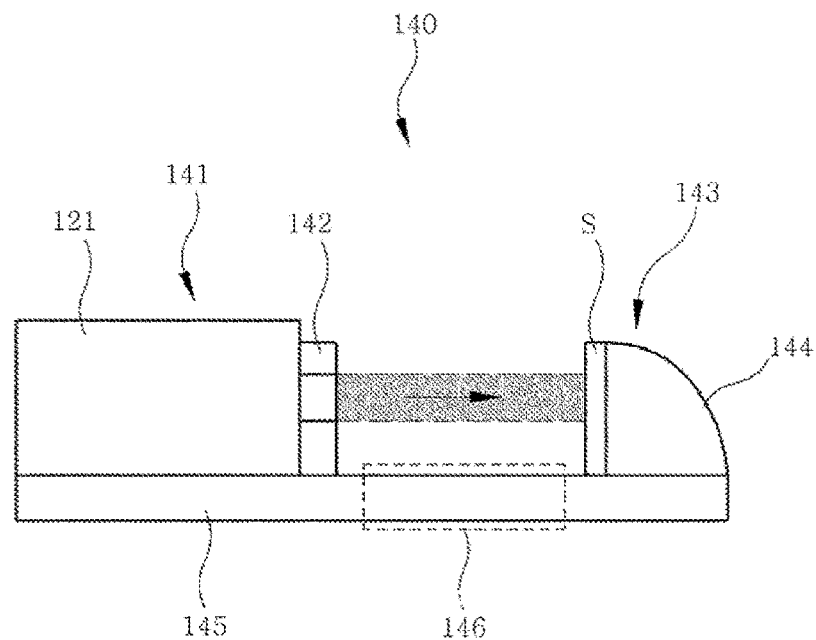
FIG. 36 is a view when an X-ray generator is mounted on the second body of the radiographing body of FIG. 32.
Figure 37:
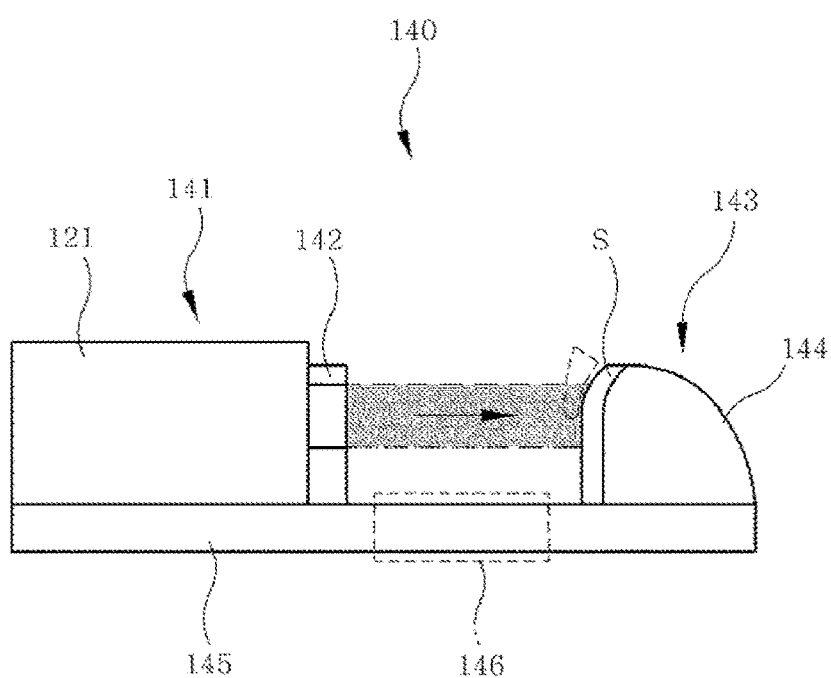
FIG. 37 is a view showing a handy type X-ray radiography device having a curved X-ray sensing unit of the radiographing body of FIG. 32.

In detail, FIG. 32 shows a radiographing body of the X-ray radiography device according to the embodiment of FIG. 9 and FIG. 33 shows the radiographing body of FIG. 32 with first and second bodies moved. Further, FIG. 34 shows a case when an X-ray generator is mounted on the first body of the radiographing body shown in FIG. 32 and FIG. 35 shows radiography using the radiographing body shown in FIG. 34. Further, FIG. 36 shows a case when an X-ray generator is mounted on the second body of the radiographing body shown in FIG. 32 and FIG. 37 shows a handy type X-ray radiography device having a curved X-ray sensing unit of the radiographing body of FIG. 32.

For convenience, only the radiographing body 140 is described hereafter and the above description can be generally applied for the other components.

First, referring to FIG. 32, the radiographing body 140 includes a first body 143 that is inserted into a subject's mouth during radiography, a second body 141 that is positioned outside a subject's mouth during radiography, and a connection frame 145 that connects the bodies into a signal body.

The connection frame 145 has a front end that is inserted into the mouth of a subject together with the first body 143 and a rear end that is larger in length than width to be positioned outside a mouth of a subject. The connection frame 145 is formed in a flat shape having a width larger than the thickness at the middle portion, which is a biting section that is bit by upper and lower teeth of a subject.

The height from the bottom of the connection frame 145 to the top of the first body 143 or the second body 141 may be larger than the height from the bottom of the connection frame 145 to the top of the middle portion.

In the biting section 146, the width corresponding to the width direction of a set of teeth of a subject of is larger than the thickness, so the connection frame 145 can be kept in a stable position when the biting section is bit between teeth.

The first body 143 at the front end of the connection frame 145 and the second body 141 at the rear end of the connection frame 145 can move relative to the connection frame 145 while being aligned with each other in the longitudinal direction of the connection frame 145.

As shown in FIG. 33, the first body 143 and the second body 141 can simultaneously slide with respect to the connection frame 145. This configuration allows for easy radiography of not only the front teeth, but the back teeth of a subject, using the radiographing body 140. That is, when the second body 141 positioned outside the mouth of a subject is moved toward back teeth with the biting section 146 bit under the front teeth of the subject, the first body 143 inside the mouth is also moved and aligned with the second body 141, whereby accurate radiography can be performed.

This configuration may be achieved in various mechanical types. For example, the first body 143 and the second body 141 may be disposed to slide on rails, respectively, arranged in the width direction of the connection frame 145, and the first body 143 and the second body 141 may be slid the same distance in the same direction by a predetermined unit in the connection frame 145.

The connection frame 145 may be made of a flexible material to be transformed by pressure applied by a user, or the connection frame 145 may have a joint so that the angle between the first body 143 and the second body 141 can be controlled. The angle made between the first body 143 and the second body 141 may be less than 180 degrees. According to this configuration, it is possible to perform radiography by controlling the angle between the first body 143 and the second body 141 when it is difficult to radiograph a desired tooth with the first body 143 and the second body 141 of the radiographing body 140 aligned in a straight line. When the connection frame 145 is bent left or right from the longitudinal direction by bending the joint, the first body 143 and the second body 141 can be rotated with respect to the connection frame 145 so that the X-ray generator and the X-ray sensing unit are aligned to face each other.

The X-ray generator is disposed at any one of the first body 143 and the second body 141 and the X-ray sensing unit is disposed at the other one. For example, an X-ray generator G may be disposed at the first body 143 and an X-ray sensing unit S may be disposed at the second body 141, as shown in FIG. 32. The position of the biting section 112 may be determined in consideration of the size of the first body 143 that is inserted into a mouth or the second body 141. A collimator 142 that controls an X-ray radiation area may be disposed on the side through which an X-ray is radiated of the X-ray generator G. The X-ray sensing unit S includes an X-ray sensor and is supported by a sensor support unit 144, and the X-ray sensing unit S may be selectively equipped with X-ray sensors having various sizes, depending on the size of the area to be radiographed. Further, a control circuit for controlling the X-ray generator G and a radiograph-processing circuit for processing electrical signals received from the X-ray sensing unit S may be disposed inside the connection frame 145 or the sensor support unit 144 that functions as a case for the first body 143 or the second body 141.

FIG. 34 shows a case when an X-ray generator is disposed at the first body. In FIG. 34, (a) shows a side of the radiographing body 140 and (b) shows the collimator 143. The collimator 142 is disposed on the path through which an X-ray radiated from the X-ray generator at the first body 143 travels and controls the size of an area O that transmits the X-ray, thereby controlling an X-ray radiation area on a tooth. A controller for the collimator 142 may be disposed at the connection frame 145, the first body 143, or the second body 141 in order to control the collimator 142 from the outside even if the collimator 142 is inserted in a mouth.

The second body 141 may further include a battery B. The battery B may be a battery pack and detachably mounted on the second body 141, or may be formed in a built-in type to be chargeable.

FIG. 35 is a view schematically showing radiography using the radiographing body. (a) shows radiography with the first body 143, which is equipped with the X-ray generator G, inserted in a mouth. The biting section 146 of the connection frame 145 is bit and supported between the upper and lower teeth of a subject.

The second body 141 that is positioned outside a mouth may further include a laser display 147 that radiates an X-ray to the mouth and displays an X-ray radiation area on the surfaces of the lips of a subject. The laser display 147 may display a laser pattern L, which shows the area where an X-ray is substantially radiated, in cooperation with the collimator 142.

FIG. 36 shows a case when an X-ray generator is disposed at the second body. As shown in this figure, the X-ray generator 121 may be disposed at the second body 141, in which the collimator 142 is disposed on a side, which faces the first body 143, of the second body 141. Further, an X-ray sensing unit S that receives an X-ray passing through a subject is disposed on the first body 143, and the X-ray sensing unit S may include an X-ray sensor and may be supported by a sensor support unit 144 that constitutes the first body 143 with the X-ray sensor S. The second body 141 that is positioned outside a mouth may further include a laser display 147 that radiates an X-ray into the mouth and displays an X-ray radiation area on the surfaces of the lips L of a subject. The laser display 147 may display a laser pattern L, which shows the area where an X-ray is substantially radiated, in cooperation with the collimator 142.

FIG. 37 shows a curved X-ray sensing unit. As shown in the figure, the first body 143 includes a curved X-ray sensing unit S. The curved X-ray sensing unit S may be curved to fit to the outline of the inner side of a tooth. The sensor support unit 144 is formed to fit to the shape of the curved X-ray sensing unit S and supports the curved X-ray sensing unit S. As a modified example, the curved X-ray sensing unit S may be bent to fit to the outline of the inner side of a tooth by pressure. In this case, the sensor support unit 144 may be made of a material that is elastically transformed with transformation of the curved X-ray sensing unit S.

Although embodiments of the present invention were described above, they are provided only for those skilled in the art to easily achieve the present invention and the present invention should not be construed as being limited to the embodiments.

INDUSTRIAL APPLICABILITY

The prevent invention can be used for medical X-ray radiography devices, particularly, dental X-ray radiography devices.

The invention claimed is:
1. An X-ray radiography device comprising:
a radiographing body including an X-ray generator; and
a variable arm relatively changing a position and a direction of the radiographing body with respect to a temporarily fixed position,
wherein the variable arm includes:
a variable connection member configured to be changed in length or direction by an external force;
a fixed end configured to be an end of the variable connection member and fixed at at least the temporarily fixed position;
a free end configured to be located in an opposite end to the fixed end, to be connected to the radiographing body, and to be changed in position and direction relative to the fixed end with transformation of the variable connection members; and
a cable;
wherein the variable connection member is a variable pipe being partially freely changeable by the external force and has a space through which the cable passes.

2. The X-ray radiography device of claim 1, wherein the variable pipe includes a plurality of gooseneck arms having different thicknesses and being connected to each other.

3. The X-ray radiography device of claim 2, wherein the plurality of gooseneck arms include:
a first plurality of gooseneck arm reinforced by a first reinforcing layer made of a metal or a synthetic resin having a first thickness (t1) (t1>0) on an inner side thereof; and
a second plurality of gooseneck arm reinforced with a second reinforcing layer made of the metal or the synthetic resin having a second thickness (t2) (t1>t2>0) on an inner side thereof.

4. The X-ray radiography device of claim 1, wherein a flexibility of the variable connection member increases along a direction from the fixed end to the free end.

5. The X-ray radiography device of claim 1, wherein the variable connection member is a multi-stepped arm including multi-stepped pipes having different diameters to be stretched or contracted for a length adjustment.

6. The X-ray radiography device of claim 1, further comprising:
a fixed body connected to the fixed end, to be fixed to an external structure, and having a power supply therein, and a cable connecting the fixed body and the radiographing body to each other and connected through an inside space of the variable connection member.

7. The X-ray radiography device of claim 6, wherein the free end is separable from the radiographing body, the fixed end is separable from the fixed body, and the variable connection member is longitudinally partially open or cut to take out the cable.

8. The X-ray radiography device of claim 7, wherein when the variable connection member is separated from the cable, the cable is put into the fixed body.

9. The X-ray radiography device of claim 1, further comprising a cable exit that is disposed at the fixed end in order to pull a cable out through the variable connection member.

10. The X-ray radiography device of claim 1, further comprising a clamp connected to the fixed end and to be fixed to an external structure.

11. The X-ray radiography device of claim 1, further comprising a body support connected to the fixed end and placed on a portion of a body of a patient to be radiographed.

12. The X-ray radiography device of claim 11, wherein the body support is a shoulder support or a headrest.

13. The X-ray radiography device of claim 1, the X-ray generator includes a field emission type of electron emitter using a nano-scaled emitter.

14. The X-ray radiography device of claim 1, wherein the radiographing body is detachably or rotatably connected to the variable arm.

* * * * *